United States Patent
Bourrel et al.

(10) Patent No.: US 8,921,117 B2
(45) Date of Patent: Dec. 30, 2014

(54) METHOD FOR ASSAYING HYDROCARBONS

(75) Inventors: Maurice Bourrel, Pau (FR); Jean-Michel Gras, Coarraze (FR)

(73) Assignee: Total S.A., Courbevoie (FR)

( * ) Notice: Subject to any disclaimer, the term of this patent is extended or adjusted under 35 U.S.C. 154(b) by 0 days.

(21) Appl. No.: 13/978,331

(22) PCT Filed: Jan. 3, 2012

(86) PCT No.: PCT/EP2012/050039
§ 371 (c)(1), (2), (4) Date: Jul. 3, 2013

(87) PCT Pub. No.: WO2012/093111
PCT Pub. Date: Jul. 12, 2012

(65) Prior Publication Data
US 2013/0277551 A1 Oct. 24, 2013

(30) Foreign Application Priority Data
Jan. 5, 2011 (FR) ..................... 11 50059

(51) Int. Cl.
*G01N 33/28* (2006.01)
*G01N 21/63* (2006.01)
*G01N 1/38* (2006.01)

(52) U.S. Cl.
CPC ............... *G01N 33/28* (2013.01); *G01N 1/38* (2013.01); *G01N 33/2823* (2013.01)
USPC ............. 436/139; 436/60; 436/171; 436/174; 422/82.09

(58) Field of Classification Search
USPC ........... 436/60, 139, 164, 166, 171, 174, 179; 422/82.05, 82.09
See application file for complete search history.

(56) References Cited

U.S. PATENT DOCUMENTS

| | | | |
|---|---|---|---|
| 6,230,799 B1 * | 5/2001 | Slaughter et al. | ............. 166/249 |
| 2005/0194323 A1 | 9/2005 | Ruth | |
| 2011/0260051 A1 | 10/2011 | Preudhomme | |

FOREIGN PATENT DOCUMENTS

WO 2004/029592 A1 4/2004

OTHER PUBLICATIONS

Brost, Dale F. et al.:"No-Solvent" Oil-in-Water Analysis—A Robust Alternative to Conventional Solvent Extraction Methods, Jan. 4, 2011, XP002656068, URL: http://www.oilinwatermonitors.com/pdf/No-Solvent_Oil-in-Water%20_Analysis-1.pdf [retrieved on Aug. 4, 2011].

* cited by examiner

*Primary Examiner* — Maureen Wallenhorst
(74) *Attorney, Agent, or Firm* — Harness, Dickey & Pierce, P.L.C.

(57) ABSTRACT

A method for determining the amount of hydrocarbons in a composition including hydrocarbons and water is provided. The method includes adding a chemical agent to the composition in order to form an emulsion of water and hydrocarbons, taking a sample of the emulsion and dissolving this sample in a common solvent for water and hydrocarbons in order to form a solution, and measuring the amount of hydrocarbons in the solution. An installation suitable for implementing this method is also provided.

11 Claims, 1 Drawing Sheet

METHOD FOR ASSAYING HYDROCARBONS

CROSS-REFERENCE TO RELATED APPLICATIONS

This application is a National Phase Entry of International Application No. PCT/EP2012/050039, filed on Jan. 3, 2012, which claims priority to French Patent Application Serial No. 1150059, filed on Jan. 5, 2011, both of which are incorporated by reference herein.

FIELD OF THE INVENTION

The present invention relates to a method for assaying hydrocarbons in a composition comprising hydrocarbons and water as well as to an installation suitable for applying this method.

BACKGROUND

In order to optimize extraction of hydrocarbons from an underground formation, it is known how to take material samples from the underground formation (core samples), or else use so-called "analog" porous materials, either consolidated or not, and saturate them with water and hydrocarbons thereby simulating the composition of a petroleum reservoir. Various extraction means may then be tested on these samples: water, steam, surfactants, polymers, gases . . . . During each experiment, fractions are retrieved, essentially comprising hydrocarbons mixed with water and mineral solids. By accurately assaying the amount of hydrocarbons present in each fraction, it is possible to obtain a simulation of the production history and thereby assess the efficiency of the tested extraction means.

An accurate assay of the amount of hydrocarbons in a mixture with water and possibly mineral solids is also useful during the production from the deposits. When dealing with not very viscous conventional crude oil, simple decantation or centrifugation may give the possibility of separating these hydrocarbons from the water and of thus carrying out the required assay. However, it happens that, even with not very viscous oils, persistent emulsions form and prevent accurate assaying of the produced hydrocarbon. When one is in the presence of heavy oils, the situation is even more difficult: indeed large amounts of water may be trapped with the hydrocarbons, and the closeness of the densities of water and of hydrocarbons makes gravitational separation inoperative. Moreover, the hydrocarbons tend to adhere to the walls of the containers used and/or to incorporate water.

Various long and tedious methods are presently used for allowing such an assay:
heating and evaporating water at atmospheric pressure or in vacuo, which does not solve the problem of determining the amount of water, which possibly remains trapped with the hydrocarbons;
assaying with X-rays, which requires very cumbersome apparatuses;
dilution of the hydrocarbons in a solvent such as toluene and then centrifugation for separating the water/oil emulsion: the quality of the water/oil separation is however very poor, and viewing the position of the interface is difficult.

The article *"No-solvent" Oil-in-Water Analysis, A Robust Alternative to Conventional Solvent Extraction Methods*, of Brost et al., available on the Internet site of Turner Designs, describes a method for assaying crude in water, wherein a surfactant is added to the mixture in order to make a micro-emulsion of crude in water, and a fluorescence measurement is then carried out on this micro-emulsion. However, this method requires a large amount of surfactant and is limited to the measurement of small amounts of oil (less than 1%). The calibration curve is non-linear, and the surfactant itself generates fluorescence which has to be subtracted, whence a significant background noise.

Therefore there exists a real need for developing an improved and simplified method allowing the assay of hydrocarbons mixed with water, which may notably be applied reliably to heavy oils and without any limitation to a measurement of small amounts of hydrocarbons.

SUMMARY

The invention firstly relates to a method for determining the amount of hydrocarbons in a composition comprising hydrocarbons and water, comprising:
adding a chemical agent to the composition in order to form an emulsion of water and hydrocarbons;
taking a sample from the emulsion and dissolving this sample in a common solvent for water and hydrocarbons in order to form a solution;
measuring the amount of hydrocarbons in the solution.

According to an embodiment, the measurement of the amount of hydrocarbons in the solution is carried out by UV spectrometry. According to an embodiment, the chemical agent is a solution comprising a base, preferably soda, or one or more surfactant compounds, or a mixture thereof. According to an embodiment, the method comprises a step of diluting the system with distilled water, in particular a dilution down to a salt concentration of the aqueous phase of less than or equal to 20 g/l. According to an embodiment, the common solvent for water and hydrocarbons is tetrahydrofurane or dimethylsulfoxide.

The invention also relates to a method for producing hydrocarbons, comprising:
extraction and retrieval of a production stream from an underground formation containing hydrocarbons;
sampling a composition comprising hydrocarbons and water stemming from the production stream;
determining the amount of hydrocarbons in said composition according to the method described above.

The invention also relates to a method for simulating the retrieval of hydrocarbons, comprising:
provision of a porous material block containing hydrocarbons;
injection into the porous material block of an agent for recovering hydrocarbons;
retrieval of one or several fractions comprising hydrocarbons and water at the exit of the porous material block; and
determining the amount of hydrocarbons in each fraction according to the method described above.

The invention also relates to an installation for determining the amount of hydrocarbons in a composition comprising hydrocarbons and water, comprising, from upstream to downstream:
means for adding a chemical agent into the composition, the chemical agent being suitable for forming an emulsion of water and hydrocarbons;
a line for collecting an emulsion sample;
means for adding a common solvent for water and hydrocarbons into the emulsion sample;
a line for collecting a solution;
means for measuring the amount of hydrocarbons in the solution.

According to an embodiment, the means for measuring the amount of hydrocarbons in the solution comprise an UV spectrometer. According to an embodiment, the means for adding a chemical agent are means for adding a solution comprising a base, preferably soda, or one or more surfactant compounds, or a mixture thereof. According to an embodiment, the means for adding a common solvent for water and hydrocarbons are means for adding tetrahydrofurane or dimethylsulfoxide. According to an embodiment, the installation comprises a first chamber suitable for mixing the chemical agent with the composition in order to form the emulsion, and a second chamber suitable for mixing the emulsion sample with the solvent in order to form the solution. According to an embodiment, the installation comprises a sampler suitable for providing the composition.

With the present invention, it is possible to overcome the drawbacks of the state of the art. More particularly it provides an improved and simplified method for determining the amount of hydrocarbons in mixture with water. This method is notably applied reliably to heavy oils and is not limited to the measurement of small amounts of hydrocarbons. This is accomplished by the use of an emulsification step, with which a homogeneous mixture of hydrocarbons and water may be obtained; of a step of taking an emulsion sample, which is representative of the composition as a whole, considering the homogeneity of the latter; and of a dissolution step in a solvent, with which a solution may be obtained in which the hydrocarbons and water are dispersed in the solvent at a molecular level, which allows direct measurement of the amount of hydrocarbons in this solution.

According to certain particular embodiments, the invention also has one or preferably more of the advantageous features listed below.

- The method according to the invention may be implemented manually or by using an integrated apparatus (installation according to the invention) which is optionally portable. The whole procedure may be automated.
- The method according to the invention is fast (typically about 5 minutes).
- The method according to the invention overcomes the difficulties related to the heterogeneity of the assayed composition, and notably to the presence of trapped water or gas bubbles.
- The method according to the invention neither requires large amounts of chemicals nor complex and costly equipments. In particular, the actual measurement of the hydrocarbon content may be carried out with commercially available apparatuses (UV spectrometer for example).

DETAILED DESCRIPTION

Figure 1:
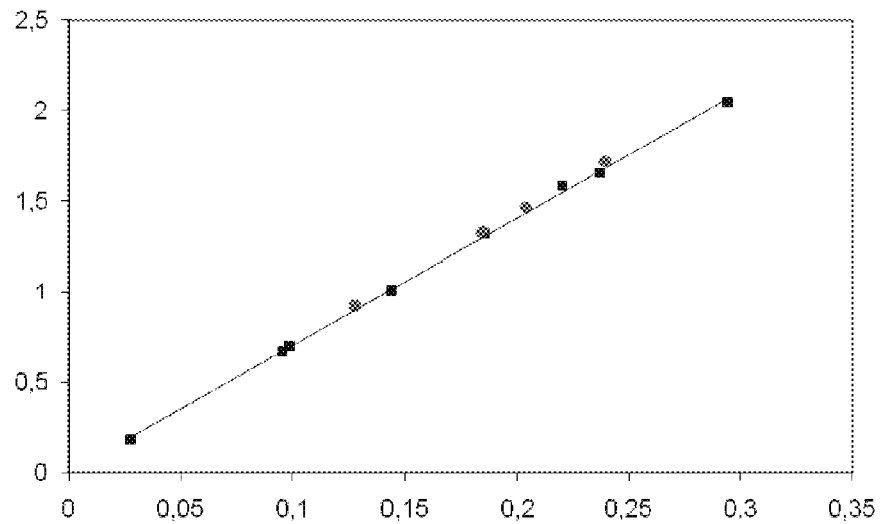
FIG. 1 provides the correspondence between the UV absorbance measurement (in ordinates, without any units) and the crude oil mass concentration (abscissae, in %) in tetrahydrofurane. The square symbols represent the calibration of the crude oil without any water, and the circle symbols represent the calibration of the crude oil in the presence of water. The water/crude oil ratio varies from about 9 to 1. See Example 1 below.

The invention is now described in more detail and in a non-limiting way in the following description. The invention applies to any composition comprising non-gaseous hydrocarbons and water. The composition may also optionally comprise gaseous hydrocarbons, but the latter are intended to be discharged early during the method and are therefore not assayed.

The invention is particularly useful for determining the amount of so-called heavy oils. Therefore, according to an embodiment, the (non-gaseous) hydrocarbons of the composition have an API degree (density measured according to the API method) of less than or equal to 10 and/or comprise a mass proportion of molecules comprising at least 12 carbon atoms, greater than or equal to 80%, preferably greater than or equal to 90% or 95%. The hydrocarbons/water mass ratio may vary from $5 \times 10^{-5}$ (determining the amount of crude dispersed in water) to 10. The composition may also contain other compounds, and notably mineral solid particles. At least one portion of the mineral solid particles may be separated from the composition by decantation or filtration before the step of adding a chemical.

In a first phase, the invention therefore provides the addition of a chemical agent to the composition in order to form an emulsion of water and hydrocarbons. The chemical agent may be a solution comprising one or more surfactant compounds. But this may also be, according to a particularly simple embodiment, an alkaline solution, such as a soda solution. Indeed, a base (such as soda) may react with the naphthenic acids present in the hydrocarbons and form surfactant compounds in situ. Soda may be replaced with another base such as potash, ammonia or sodium carbonate etc.

If on the other hand (or as an addition), a supplement of surfactant compound is used, notably for not very acid oils, the surfactant compound(s) have to be selected so as not to perturb the final step of measuring the amount of hydrocarbons. For example in the case of measurement of UV absorbance, the surfactant compounds must be essentially non-absorbent in the UV spectrum. The chemical agent should be mixed with the composition until the emulsion is obtained, either manually or preferably, by using mechanical mixing means (stirrer with paddles, magnetic stirrer, vortex stirrer, or others).

The nature and the amount of the chemical agent are adapted according to the nature of the composition so as to allow formation of a homogeneous emulsion. The concentration of the chemical agent may vary between 0.05% and 3% by mass. The formed emulsion should be of the oil-in-water type, and therefore have good fluidity. By observing it visually with stirring, it is then possible to appreciate its homogeneity.

In a second phase, the invention provides the taking of a sample of the emulsion, which is representative of the global emulsion, and then dissolving this sample in a common solvent for water and hydrocarbons in order to form a solution. By sampling, it is possible to limit the amount of solvent used while obtaining a sufficiently diluted hydrocarbon solution so as to be able to carry out a measurement of the hydrocarbon concentration while avoiding saturation of the measurement apparatus. Depending on the solvent, the rate of dilution by the solvent may vary from 1 to 10.

It is considered that a product is a solvent for water and for hydrocarbons when, at room temperature, and at ambient pressure, the solubility of water in this product is greater than or equal to 30% by volume and the solubility of the hydrocarbons in this product is greater than or equal to 30% by volume. If the water contains salt, at a concentration greater than typically 20 g/L, solubilization of the water in the solvent may become insufficient and separation of the phases may occur. The method requires an additional step in order to adapt to this situation. This additional step consists in diluting the system with distilled water so as to reduce the salinity to a value of less than 20 g/L.

The method of the invention may further include a step of determining the amount of salt in the aqueous phase, prior to the step of dilution with distilled water. A highly efficient common solvent for water and hydrocarbons is tetrahydrofurane, but, without this list being limiting, it is possible to use other solvents such as dimethylsulfoxide, dimethylformamide, dimethylacetamide etc.

If mineral solid particles are still present in the solution, they generally decant easily because of the disappearance of the aqueous phase in which these particles are generally suspended and are therefore no longer a nuisance for the measurement. Alternatively, provision may be made for filtration, if required. The possibly present gas is generally also discharged during this step.

In a third phase, a direct measurement of the amount of hydrocarbons in the solution is carried out. A particularly simple method consists of carrying out an absorbance measurement of the solution in the UV range, by using a spectrometer. This requires preliminarily calibration of the spectrometer with samples of hydrocarbons in the solvent at various concentrations. By completely analyzing the UV spectrum of the hydrocarbon, it is possible to select wavelengths producing different absorbances. Depending on whether the samples are strongly concentrated or strongly diluted, wavelengths may be selected, which produce low or strong absorbances, respectively, allowing enhanced accuracy.

It is remarkable that the presence of water in the solution in which the measurement is carried out does not perturb said measurement. This is confirmed by FIG. 1, which shows a superposition of the calibration curves of a crude oil in tetrahydrofurane at a wavelength of 408 nm, with and without water (see Example 1). Further, the calibration curve is linear over a wide concentration range if the dilution of the emulsion in the solvent has been properly adjusted, which gives the possibility of carrying out a particularly reliable measurement.

The method of the invention is particularly useful for determining the amount of hydrocarbons in fractions obtained during a simulation experiment for recovering hydrocarbons in a porous material block. It may also be applied to determining the amount of hydrocarbons in a production stream. The method of the invention may be applied by means of an installation according to the invention.

Figure 2:
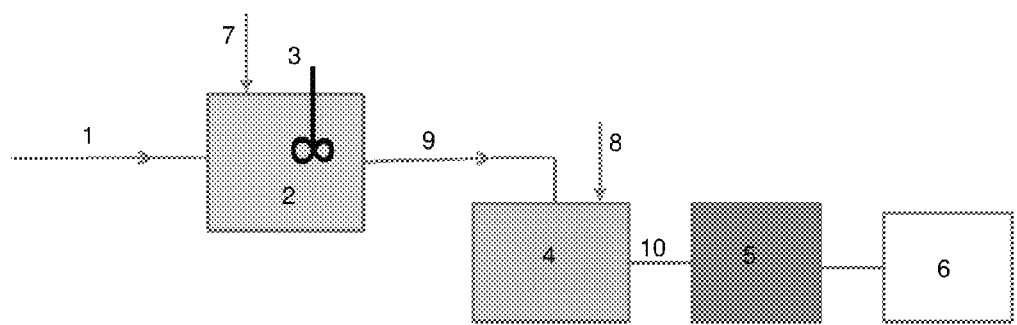
FIG. 2 is a schematic illustration of an embodiment of the installation according to the invention.

With reference to FIG. 2, this installation may comprise means 1 for supplying a composition comprising hydrocarbons and water, which may for example comprise manual composition supply means or means for collecting and taking samples in a production stream or in recovered fractions during a simulation experiment for recovering hydrocarbons in a porous material block. It also comprises means 7 for adding a chemical agent, connected to a tank of chemical agent. The composition supply means 1 feed a first chamber 2 (or emulsification chamber), advantageously provided with mixing means 3. The chemical agent addition means 7 may either be connected to the first chamber 2 or to the composition supply means 1 upstream from the latter.

At the outlet of the first chamber 2, provision is made for a line 9 for collecting emulsion samples, provided with sampling means, which feeds a second chamber 4 (or dissolution chamber). Means 8 for adding solvent either feed the second chamber 4 or the line 9 for collecting emulsion samples upstream from the latter. The second chamber 4 is advantageously provided with mixing means (not shown).

At the outlet of the second chamber 4, provision is made for a line 10 for collecting solution, which feeds means 5 for measuring the amount of hydrocarbons in the solution (for example a UV spectrometer). A computer 6 allows acquisition of the measurement et and optional control of the whole of the installation. The installation is advantageously provided with a set of valves, discharge means and cleaning means, not shown.

EXAMPLES

The following examples illustrate the invention without limiting it.

Example 1

Viscous crude oil P1 (10,000 cP at room temperature) is dissolved in tetrahydrofurane (THF) at a concentration of 0.15% by weight. The absorption spectrum is determined in the wavelength range 190-1,100 nm. A secondary absorption peak appears at 408 nm, a wavelength which is retained for the assay.

A range of solutions of crude in THF is prepared in the 0.1 wt %-0.3 wt % concentration range. The absorbance A, measured at 408 nm, is plotted versus the concentration $C_B$ in FIG. 1. The absorbance varies linearly with the concentration (regression coefficient of 0.9989). The thereby obtained line of equation $A=7.00119\, C_B$ (1) forms the calibration for assaying the relevant crude.

The effect of the presence of water in the crude+THF mixture was studied. Table 1 gives the results of the measurement of absorbance A in the presence of water to be compared with the absorbance calculated from equation (1) above in the absence of water. It shows that the absorbance measurement is not significantly affected by water (<3%), and therefore that equation (1) may be used for calculating the concentration of crude. The representative points of these calculations are plotted (red circles) in FIG. 1.

TABLE 1

| Crude weight % | $H_2O$ weight % | THF weight % | $H_2O$/crude weight/ weight | Measured absorbance 408 nm | Calculated absorbance 408 nm |
|---|---|---|---|---|---|
| 0.1279 | 1.17 | 98.71 | 9.1 | 0.9220 | 0.8968 |
| 0.185 | 0.75 | 99.06 | 4.1 | 1.3230 | 1.2972 |
| 0.2038 | 0.48 | 99.32 | 2.3 | 1.4652 | 1.4290 |
| 0.2398 | 0.25 | 99.51 | 1.0 | 1.7213 | 1.6815 |

An experiment for retrieving this oil trapped in a core sample of porous medium was conducted by injecting water+chemical additives. The produced fluids (crude+water) are collected in a fraction collector. A mass of 2 g of aqueous 0.4% soda solution is placed beforehand in each collector tube so as to limit adherence of the crude to the walls of the tube and to facilitate subsequent emulsification of the mixture. The whole is weighed.

After collecting the effluents, the tubes are weighed and a known mass of 0.4% soda solution is added. The tubes are then stirred manually and a fluid emulsion is formed. As an example, the masses of the collected effluents in a few tubes as well as the total amount of added soda solution are given in Table 2. A fraction of the emulsion is then taken from each tube and poured into new test tubes containing tetrahydrofurane. The whole is again weighed. After stirring, a limpid solution is obtained, which is assayed by UV spectrometry at 408 nm. The concentrations of crude are calculated by means of the calibration line of FIG. 1 (Equation (1)). The bitumen content in the initial collection tube is then calculated by taking into account the dilution factors by the soda solution and tetrahydrofurane.

TABLE 2

|  | Collection Tube | | | |
| --- | --- | --- | --- | --- |
|  | A | B | C | D |
| Initial mass of effluents + soda (g) | 9.8267 | 10.2201 | 9.9678 | 10.2573 |
| Added soda mass (g) | 5.2000 | 5.1800 | 5.2350 | 5.1716 |
| Sampled emulsion mass (g) | 0.2985 | 0.3661 | 0.5361 | 0.8167 |
| Emulsion + THF mass (g) | 44.5247 | 44.6915 | 44.6146 | 44.5103 |
| Measured absorbance (408 nm) | 1.5662 | 1.0456 | 0.7683 | 0.6219 |
| Crude oil concentration In the collection tube (weight %) | 75.39 | 39.59 | 20.59 | 10.54 |

Example 2

A solution of not very viscous crude oil P2 (3 cP at room temperature) at 0.15 wt % in tetrahydrofurane was studied in spectroscopy between 190 and 1,100 nm. An absorption peak appears at 263 nm, for which the absorbance is close to 1.9. In order to be able to assay more concentrated solutions without additional dilution, the calibration was carried out by also measuring the absorbance at 3 other different wavelengths: 325, 350 and 375 nm. A range of solutions of crude in THF, the concentration of which varies from 0.01% to 1% by weight, led to 4 calibration curves at the selected wavelengths.

The results are given in Table 3.

TABLE 3

| C wt/wt % | A at 263 nm | A at 325 nm | A at 350 nm | A at 375 nm |
| --- | --- | --- | --- | --- |
| 0.011 | 0.1522 | 0.0437 | 0.0263 | 0.015 |
| 0.0468 | 0.6093 | 0.1815 | 0.1137 | 0.0702 |
| 0.0853 | 1.0496 | 0.3041 | 0.1885 | 0.1128 |
| 0.1556 | 1.8776 | 0.5611 | 0.3496 | 0.2098 |
| 0.3313 |  | 1.1671 | 0.7305 | 0.4404 |
| 0.5178 |  | 1.7951 | 1.1354 | 0.6833 |
| 0.973 |  |  | 2.0665 | 1.2595 |

The absorbance A varies linearly with the concentration of crude $C_B$:
$A = \alpha C_B$, with $C_B$ in % by weight (Table 4).

TABLE 4

|  | Wavelength (nm) | | | |
| --- | --- | --- | --- | --- |
|  | 263 | 325 | 350 | 375 |
| α | 12.186 | 3.494 | 2.1472 | &.3037 |
| Regression coefficient | 0.9986 | 0.9996 | 0.9994 | 0.9997 |

The calibration line at 263 nm is indeed used for concentrations below 0.15%. For higher contents, other lines may be used, while making sure that the absorbance levels remain below 2. If this is not the case, an additional dilution should be carried out.

An emulsion of crude in salty water (10 g/l NaCl and 4 g/l NaOH) was prepared for various samples in an aqueous phase/crude oil mass ratio of 10/1. The absorbance was measured and compared with the one predicted from the data in Table 5. It is seen that the presence of water perturbs by less than 3% the measurement of the concentration of hydrocarbons.

TABLE 5

| C wt/wt % | 0.0468 | 0.0801 | 0.1577 |
| --- | --- | --- | --- |
| A measured at 263 nm | 0.58 | 1.0078 | 1.8895 |
| Calculated A | 0.57 | 0.976 | 1.92 |

"Measured"=in the presence of water;
"Predicted"=from the data of table 4.

Example 3

A synthetic sample was made by mixing sand and a water emulsion of not very viscous crude oil P2, with a crude oil concentration of 5.35% by weight based on the mixture, and 2.15% of water. Two samples were taken and dispersed in THF. After stirring, the sand decanted and the supernatant was assayed with the preceding method at a wavelength of 375 nm.

Concentration measured in the sample 1: 5.48% (based on the mixture).
Concentration measured in the sample 2: 5.43% (based on the mixture).

The presence of solid does not perturb the measurement of the concentration of hydrocarbons.

Example 4

An emulsion of not very viscous crude of Example 2 in salty water with 35 g/L NaCl and 6 g/L NaOH, is prepared with an aqueous phase/crude oil mass ratio of 1/1. To 0.4 g of this emulsion are added 1.2 g of distilled water. Dilution with 40 g of THF leads to a homogeneous solution.

The calculated absorbance at 325 nm is 1.677. The measured absorbance is 1.722, in very good agreement with the predicted value.

By diluting the emulsion sample with distilled water, it is therefore possible to apply the method to systems, wherein the electrolyte content of the water is high (typically greater than 20 g/L). At these salinities, indeed, direct dilution with THF leads to a separation of the phases of the system, and not to the homogeneous solution allowing the concentration of crude oil to be measured by UV.

The invention claimed is:
1. A method for determining the amount of hydrocarbons in a composition comprising hydrocarbons and water, comprising:
adding a surfactant or a base/alkaline solution to the composition in order to form an emulsion of water and of hydrocarbons;
taking a sample from the emulsion and dissolving this sample in a common solvent for water and hydrocarbons in order to form a solution; and
measuring the amount of hydrocarbons in the solution by UV spectrometry.
2. The method according to claim 1, further comprising diluting the solution obtained after taking the sample from the emulsion and dissolving this sample in a common solvent for water and hydrocarbons with distilled water.

3. The method according to claim 2, wherein diluting the solution with distilled water is performed to reduce the salinity of the solution to a value of less than or equal to 20 g/l.

4. The method according to claim 1, wherein the common solvent for water and hydrocarbons is tetrahydrofurane or dimethylsulfoxide.

5. A method for simulating the retrieval of hydrocarbons, comprising:
provides a porous material block containing hydrocarbons;
injecting into the porous material block an agent for recovering hydrocarbons;
retrieving one or several fractions comprising hydrocarbons and water from the porous material block; and
determining the amount of hydrocarbons in each fraction according to the method of claim 1.

6. The method according to claim 1, wherein the base/alkaline solution is a solution comprising soda.

7. A method for producing hydrocarbons, comprising:
(a) extracting and retrieving a production stream from an underground formation containing hydrocarbons;
(b) sampling a composition comprising hydrocarbons and water stemming from the production stream;
(c) determining the amount of hydrocarbons in the composition by:
adding a surfactant or a base/alkaline solution to the composition in order to form an emulsion of water and of hydrocarbons;
taking a sample from the emulsion and dissolving this sample in a common solvent for water and hydrocarbons in order to form a solution; and
measuring the amount of hydrocarbons in the solution by UV spectrometry.

8. An installation for determining the amount of hydrocarbons in a composition comprising hydrocarbons and water, comprising, from upstream to downstream:
a composition supply of a composition comprising hydrocarbons and water feeding a first chamber;
a chemical agent supply from which a surfactant or a base/alkaline solution is added into the composition, the chemical agent supply being either connected to the first chamber or to the composition supply, the surfactant or the base/alkaline solution being suitable for forming an emulsion of water and hydrocarbons;
an emulsion line for collecting an emulsion sample at the outlet of the first chamber, the emulsion line feeding a second chamber;
a solvent supply from which a common solvent is added for water and hydrocarbons into the emulsion sample, the solvent supply feeding either the second chamber or the line for collecting an emulsion sample;
a solution line for collecting a solution at the outlet of the second chamber;
and the solution line feeding
a measurer comprising a UV spectrometer for measuring the amount of hydrocarbons in the solution.

9. The installation according to claim 8, wherein the solvent supply adding a common solvent for water and hydrocarbons is a supply for adding tetrahydrofurane or dimethylsulfoxide.

10. The installation according to claim 8, comprising a first chamber, suitable for mixing the surfactant or the base/alkaline solution with the composition in order to form the emulsion, and a second chamber, suitable for mixing the emulsion sample with the solvent in order to form the solution.

11. The installation according to claim 8, wherein the chemical agent supply adding a surfactant or a base/alkaline solution is a supply adding a solution comprising soda.

* * * * *